(12) United States Patent
Ikeda et al.

(10) Patent No.: US 7,939,695 B2
(45) Date of Patent: May 10, 2011

(54) PRODUCTION PROCESS OF NUCLEUS-HALOGENATED METHYLBENZYL ALCOHOL

(75) Inventors: Haruhiko Ikeda, Kawasaki (JP); Hideo Miyata, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 570 days.

(21) Appl. No.: 11/917,956

(22) PCT Filed: Jun. 12, 2006

(86) PCT No.: PCT/JP2006/312193
§ 371 (c)(1),
(2), (4) Date: Dec. 18, 2007

(87) PCT Pub. No.: WO2006/137348
PCT Pub. Date: Dec. 28, 2006

(65) Prior Publication Data
US 2010/0145106 A1    Jun. 10, 2010

Related U.S. Application Data

(60) Provisional application No. 60/695,429, filed on Jul. 1, 2005.

(30) Foreign Application Priority Data

Jun. 22, 2005    (JP) ................................ 2005-182323

(51) Int. Cl.
C07C 29/14 (2006.01)
(52) U.S. Cl. ...................................................... 568/814
(58) Field of Classification Search .................. 568/814
See application file for complete search history.

(56) References Cited

U.S. PATENT DOCUMENTS

| | | | |
|---|---|---|---|
| 4,551,546 A | 11/1985 | Punja | |
| 6,624,336 B1 * | 9/2003 | Sasaki et al. | 568/812 |
| 6,828,467 B2 | 12/2004 | Miura et al. | |
| 6,894,195 B2 | 5/2005 | Jones et al. | |
| 2004/0010167 A1 | 1/2004 | Miura et al. | |
| 2004/0063993 A1 | 4/2004 | Jones et al. | |
| 2005/0054886 A1 | 3/2005 | Jones | |

FOREIGN PATENT DOCUMENTS

| | | |
|---|---|---|
| JP | 56-97251 A | 5/1981 |
| JP | 2000-256244 A | 9/2000 |
| JP | 2002-173455 A | 6/2002 |
| JP | 2004-512319 T | 4/2004 |
| JP | 2004-512320 T | 4/2004 |
| WO | 0226678 A2 | 4/2002 |

OTHER PUBLICATIONS

Shizheng Zhu et al., "A new route to 2,3,5,6-tetrafluoroterephthal aldehyde and its chemical transformation", Journal of Fluorine Chemistry, 2004, pp. 451-454, vol. 125, No. 3.

Stefan Peterli et al., "7. Nitrostyrene Derivatives of Adenosine 5'-Glutarates Modified with an Alkyl Spacer and Their Inhibitory Activity on Epidermal Growth Factor Receptor Protein Tyrosine Kinase", Helvetica Chimica ACTA, 1994, pp. 59-69, vol. 77.

* cited by examiner

*Primary Examiner* — Sikarl A Witherspoon
(74) *Attorney, Agent, or Firm* — Sughrue Mion, PLLC

(57) ABSTRACT

The present invention provides an industrially advantageous process for preparing nucleus-halogenated methylbenzyl alcohol which is a useful substance as a raw material, an intermediate for manufacturing medicines, agricultural chemicals, etc. The process of the present invention for preparing nucleus-halogenated methylbenzyl alcohol represented by the following formula (II) includes hydrogenating nucleus-halogenated benzene dicarbaldehyde represented by the following formula (I);

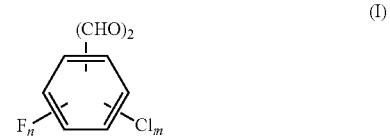

wherein m is an integer of 0 to 3, and n is an integer of 1 to 4, with the proviso that m+n is an integer of 1 to 4,

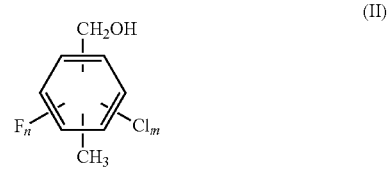

wherein m and n are the same as those in the formula (I).

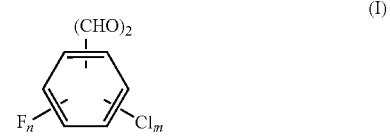

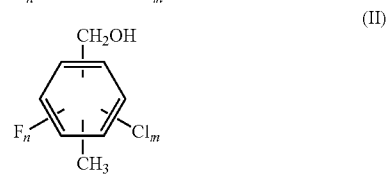

17 Claims, No Drawings

PRODUCTION PROCESS OF NUCLEUS-HALOGENATED METHYLBENZYL ALCOHOL

CROSS REFERENCE OF RELATED APPLICATION

This application is an application filed under 35 U.S.C. Section 111(a) claiming benefit pursuant to 35 U.S.C. Section 119(e)(1) of the filing date of Provisional Application 60/695,429 on Jul. 1, 2005, pursuant to 35 U.S.C. Section 111(b).

TECHNICAL FIELD

The present invention relates to a process for preparing nucleus-halogenated methylbenzyl alcohol by hydrogenating nucleus-halogenated benzene dicarbaldehyde to convert one aldehyde group of the nucleus-halogenated benzene dicarbaldehyde into a methyl group and the other aldehyde group thereof into an alcohol group particularly in a solvent and in the presence of a catalyst.

BACKGROUND ART

Nucleus-halogenated methylbenzyl alcohol is a useful substance as a raw material, an intermediate or the like for manufacturing medicines, agricultural chemicals, etc. For example, in Japanese Patent Laid-Open Publication No. 97251/1981, it is described that esters formed by the reaction with cyclopropanecarboxylic acids are useful as substances having excellent insecticidal action.

As a process for preparing nuclear fluorinated methylbenzyl alcohol, there has been heretofore disclosed, for example, a process comprising allowing a pentafluorobenzyl alcohol derivative, an alcohol moiety of which has been protected, to react with methyllithium to convert the derivative into a 4-methyltetrafluorobenzyl alcohol derivative (Japanese Patent Laid-Open Publication No. 256244/2000), a process comprising halogenating 1,4-bis(hydroxymethyl)-2,3,5,6-tetrafluorobenzene to obtain 4-(halomethyl)-2,3,5,6-tetrafluorobenzyl alcohol and then hydrogenating it to derive 4-methyl-2,3,5,6-tetrafluorobenzyl alcohol (Japanese Patent Laid-Open Publication No. 512319/2004) or a process comprising converting 4-methyl-2,3,5,6-tetrafluorobenzylamine, which has been obtained by hydrogenation of 4-methyl-2,3,5,6-tetrafluorobenzonitrile, into 4-methyl-2,3,5,6-tetrafluorobenzyl alcohol (Japanese Patent Laid-Open Publication No. 512320/2004). However, it is hard to say that these processes are industrially useful because expensive reducing agents are used, their steps are long, etc. Further, a process for preparing 4-methyl-2,3,5,6-tetrafluorobenzyl alcohol by hydrogenating a hydroxyl group of one side of the aforesaid 1,4-bis(hydroxymethyl)-2,3,5,6-tetrafluorobenzene has been also disclosed (Japanese Patent Laid-Open Publication No. 173455/2002).

DISCLOSURE OF THE INVENTION

It is an object of the present invention to provide a process for preparing a nucleus-halogenated methylbenzyl alcohol compound which is useful as a raw material or an intermediate for manufacturing medicines, agricultural chemicals and the like.

The present inventors have earnestly studied, and as a result, they have found that the above problem can be solved by using nucleus-halogenated benzene dicarbaldehyde as a raw material and converting one aldehyde group of the material into a methyl group and the other aldehyde group into a hydroxymethyl group. Based on the finding, the present invention has been accomplished.

The present invention includes the following matters.

(1) A process for preparing nucleus-halogenated methylbenzyl alcohol represented by the following formula (II), comprising hydrogenating nucleus-halogenated benzene dicarbaldehyde represented by the following formula (I);

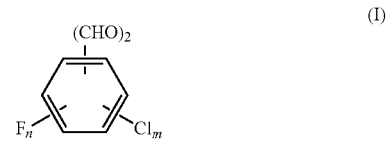

wherein m is an integer of 0 to 3, and n is an integer of 1 to 4, with the proviso that m+n is an integer of 1 to 4,

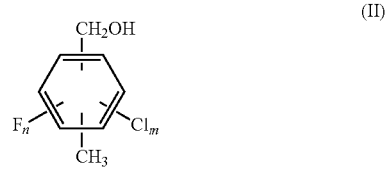

wherein m and n are the same as those in the formula (I).

(2) The process for preparing nucleus-halogenated methylbenzyl alcohol as stated in (1), wherein the nucleus-halogenated benzene dicarbaldehyde is represented by the following formula (III):

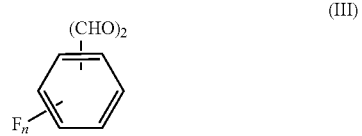

wherein n is an integer of 1 to 4, and the nucleus-halogenated methylbenzyl alcohol formed is represented by the following formula (IV):

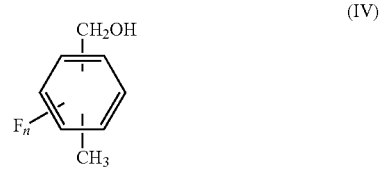

wherein n is the same as that in the formula (III).

(3) The process for preparing nucleus-halogenated methylbenzyl alcohol as stated in (1), wherein the nucleus-halogenated benzene dicarbaldehyde is tetrafluorobenzene dicarbaldehyde represented by the following formula (V),

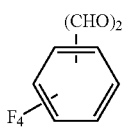
(V)

and the nucleus-halogenated methylbenzyl alcohol formed is tetrafluoromethylbenzyl alcohol represented by the following formula (VI).

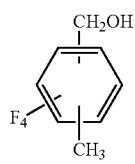
(VI)

(4) The process for preparing nucleus-halogenated methylbenzyl alcohol as stated in (3), wherein the tetrafluorobenzene dicarbaldehyde represented by the formula (V) is 2,3,5,6-tetrafluorobenzene-1,4-dicarbaldehyde, and the tetrafluoromethylbenzyl alcohol represented by the formula (VI) is 2,3,5,6-tetrafluoro-4-methylbenzyl alcohol.

(5) The process for preparing nucleus-halogenated methylbenzyl alcohol as stated in any one of (1) to (4), wherein the hydrogenation reaction is carried out in a solvent and in the presence of a catalyst.

(6) The process for preparing nucleus-halogenated methylbenzyl alcohol as stated in (5), wherein the catalyst is a catalyst containing at least one metal selected from the group consisting of cobalt, iron, copper, nickel, platinum, palladium, rhodium and rhenium, and the hydrogenation reaction is carried out using hydrogen.

(7) The process for preparing nucleus-halogenated methylbenzyl alcohol as stated in (6), wherein the catalyst is a sponge cobalt-based catalyst or a sponge nickel-based catalyst.

(8) The process for preparing nucleus-halogenated methylbenzyl alcohol as stated in (6), wherein the catalyst is a supported cobalt-based catalyst, a supported nickel-based catalyst, a supported platinum-based catalyst, a supported palladium-based catalyst, a supported rhodium-based catalyst or a supported rhenium-based catalyst.

(9) The process for preparing nucleus-halogenated methylbenzyl alcohol as stated in any one of (5) to (8), wherein the solvent is a single solvent or a mixed solvent containing at least one substance selected from the group consisting of saturated aliphatic hydrocarbons, alicyclic hydrocarbons, aromatic hydrocarbons, alcohols, ethers of aliphatic hydrocarbons, ethers of alicyclic hydrocarbons and water.

(10) The process for preparing nucleus-halogenated methylbenzyl alcohol as stated in (9), wherein the solvent is a single solvent or a mixed solvent containing at least one substance selected from the group consisting of toluene, xylene, methanol, ethanol, dioxane, dioxolane and water.

(11) The process for preparing nucleus-halogenated methylbenzyl alcohol as stated in any one of (1) to (10), wherein the hydrogenation reaction is carried out at a hydrogen partial pressure of 0.2 to 5 MPa.

(12) The process for preparing nucleus-halogenated methylbenzyl alcohol as stated in any one of (5) to (11), wherein the amount of the solvent used in the hydrogenation reaction is in the range of 1 to 20 times by mass the amount of the nucleus-halogenated benzene dicarbaldehyde represented by the formula (I).

(13) The process for preparing nucleus-halogenated methylbenzyl alcohol as stated in any one of (6) to (12), wherein the ratio of the actual amount of absorbed hydrogen in the hydrogenation reaction to the theoretical amount of absorbed hydrogen when all the nucleus-halogenated benzene dicarbaldehyde represented by the formula (I) is hydrogenated into the nucleus-halogenated methylbenzyl alcohol represented by the formula (II) is in the range of 80 to 130%.

EFFECT OF THE INVENTION

In the preparation process of the invention, a nucleus-halogenated methylbenzyl alcohol compound can be inexpensively and efficiently obtained through simple operations, and because a by-product is hardly formed, a burden with equipment for further carrying out isolation and purification can be reduced, so that this process is industrially useful.

BEST MODE FOR CARRYING OUT THE INVENTION

The present invention is described in more detail hereinafter.

The nucleus-halogenated benzene dicarbaldehyde compound for use in the preparation process of the invention is represented by the following formula (I):

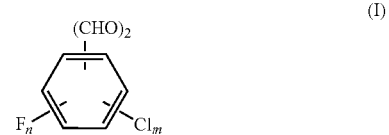
(I)

wherein m is an integer of 0 to 3, and n is an integer of 1 to 4, with the proviso that m+n is an integer of 1 to 4.

Examples of the compounds represented by the formula (I) include monofluorobenzene dicarbaldehydes, such as 2-fluorobenzene-1,4-dicarbaldehyde, monochloromonofluorobenzene dicarbaldehydes, such as 2-chloro-3-fluorobenzene-1,4-dicarbaldehyde and 2-chloro-5-fluorobenzene-1,4-dicarbaldehyde, dichloromonofluorobenzene dicarbaldehydes, such as 2,3-dichloro-5-fluorobenzene-1,4-dicarbaldehyde and 2,5-dichloro-3-fluorobenzene-1,4-dicarbaldehyde, trichloromonofluorobenzene dicarbaldehydes, such as 2,3,5-trichloro-6-fluorobenzene-1,4-dicarbaldehyde, difluorobenzene dicarbaldehydes, such as 2,3-difluorobenzene-1,4-dicarbaldehyde, 2,5-difluorobenzene-1,4-dicarbaldehyde and 2,6-difluorobenzene-1,4-dicarbaldehyde, monochlorodifluorobenzene dicarbaldehydes, such as 2-chloro-3,5-difluorobenzene-1,4-dicarbaldehyde, dichlorodifluorobenzene dicarbaldehydes, such as 2,3-dichloro-5,6-difluorobenzene-1,4-dicarbaldehyde, trifluorobenzene dicarbaldehydes, such as 2,3-5-trifluorobenzene-1,4-dicarbaldehyde, monochlorotrifluorobenzene dicarbaldehydes, such as 2-chloro-3,5,6-trifluorobenzene-1,4-dicarbaldehyde, and tetrafluorobenzene dicarbaldehydes, such as 2,3,5,6-tetrafluorobenzene-1,4-dicarbaldehyde, 2,4,5,6-tetrafluorobenzene-1,3-dicarbaldehyde and 3,4,5,6-tetrafluorobenzene-1,2-dicarbaldehyde.

Of the above compounds, preferable are tetrafluorobenzene dicarbaldehydes, and more preferable is 2,3,5,6-tetrafluorobenzene-1,4-dicarbaldehyde.

A part of the compounds enumerated above as examples of the compounds of the formula (I) are on the market and readily available. Further, the compounds of the formula (I) can be synthesized by a process described in, for example, *Journal of Fluorine Chemistry*, Vol. 125, pp. 451-454 (edited in 2004). For example, tetrafluoroisophthalonitrile, tetrafluoroterephthalonitrile, tetrachloroisophthalonitrile, tetrachloroterephthalonitrile, 2,4,6-trifluoro-5-chloroisophthalonitrile or the like is subjected to catalytic reduction to convert a nitrile group into an aldehyde group, whereby 2,4,5,6-tetrafluorobenzene-1,3-dicarbaldehyde, 2,3,5,6-tetrafluorobenzene-1,4-dicarbaldehyde, 2,4,5,6-tetrachlorobenzene-1,3-dicarbaldehyde, 2,3,5,6-tetrachlorobenzene-1,4-dicarbaldehyde, 2,4,6-trifluoro-5-chlorobenzene-1,3-dicarbaldehyde or the like can be synthesized.

The preparation process of the invention is a process for preparing nucleus-halogenated methylbenzyl alcohol compound represented by the aforesaid formula (II) by subjecting a nucleus-halogenated benzene dicarbaldehyde compound represented by the aforesaid formula (I) to hydrogenation reaction to convert one aldehyde group into a hydroxymethyl group and the other aldehyde group into a methyl group.

In the preparation process of the invention, the hydrogenation reaction is carried out using hydrogen preferably in a solvent and in the presence of a catalyst. As the catalyst, a metal catalyst is used, and a catalyst containing at least one metal selected from the group consisting of cobalt, iron, copper, nickel, platinum, palladium, rhodium and rhenium is preferably used. The catalyst may be used in the form of a metal as such, in the form of a sponge metal or in a supported form.

The sponge metal catalyst is a porous metal catalyst obtained by dissolving an alkali- or acid-soluble metal out of an alloy of an alkali- or acid-insoluble metal (e.g., nickel, cobalt) and an alkali- or acid-soluble metal (e.g., aluminum, silicon, zinc, magnesium) using an alkali or an acid, and is specifically a sponge cobalt-based catalyst or a sponge nickel-based catalyst. A modified sponge metal catalyst obtained by modifying the above sponge metal catalyst with another metal or a metal oxide is also employable, and the modified sponge metal catalyst is, for example, a molybdenum-modified sponge nickel-based catalyst or a molybdenum-modified sponge cobalt-based catalyst.

The supported catalyst is a catalyst wherein metal or metal oxide fine particles comprising one or more kinds of metal species are supported in a highly dispersed state on a carrier, such as silica, alumina, silica-alumina, activated carbon or diatomaceous earth, and is specifically a supported cobalt-based catalyst, a supported iron-based catalyst, a supported copper-based catalyst, a supported nickel-based catalyst, a supported platinum-based catalyst, a supported palladium-based catalyst, a supported rhodium-based catalyst or a supported rhenium-based catalyst.

A modified supported catalyst obtained by adding one or more kinds of the above metal species or other metal species to the above supported catalyst is also employable, and examples of such modified supported catalysts include a supported nickel-copper-alumina catalyst, a supported nickel-cobalt-alumina catalyst, a supported copper-chromium-silica catalyst and a supported palladium-rhenium-alumina catalyst.

Examples of preferred catalysts are as follows. Examples of preferred sponge metal catalysts include a sponge cobalt-based catalyst and a sponge nickel-based catalyst. Examples of preferred supported catalysts include a supported cobalt-based catalyst, a supported nickel-based catalyst, a supported palladium-based catalyst, a supported rhodium-based catalyst and a supported rhenium-based catalyst. Of these catalysts, particularly preferable are a sponge cobalt-based catalyst and a sponge nickel-based catalyst.

Next, the hydrogenation reaction in the invention is described.

The amount of the catalyst added in the reaction is not specifically restricted and varies according to the form of the catalyst, but in general, it is in the range of 0.01 to 300% by mass, preferably 0.01 to 100% by mass, particularly preferably 0.01 to 50% by mass, based on the amount of the nucleus-halogenated benzene dicarbaldehyde compound to be hydrogenated. If the catalytic amount is less than 0.01% by mass, the reaction does not proceed smoothly, and the conversion ratio is not increased. On the other hand, if the catalytic amount exceeds 300% by mass, the hydrogenation reaction proceeds further to convert both of the aldehyde groups into methyl groups, so that such an amount is undesirable.

In the hydrogenation reaction of the invention, a solvent is employed. Although the solvent is not specifically restricted, preferred examples of the solvents include saturated aliphatic hydrocarbons, alicyclic hydrocarbons, aromatic hydrocarbons, alcohols, ethers of aliphatic hydrocarbons, ethers of alicylic hydrocarbons and water. Examples of the saturated aliphatic hydrocarbons include n-hexane, n-octane and isooctane. Examples of the alicyclic hydrocarbons include cyclohexane. Examples of the aromatic hydrocarbons include benzene, toluene and xylene. Examples of the alcohols include alcohols of 1 to 4 carbon atoms, such as methanol, ethanol, n-propanol, isopropanol and n-butanol. Examples of the ethers of aliphatic hydrocarbons include diethyl ether, diisopropyl ether and methyl tertiary-butyl ether. Examples of the ethers of alicyclic hydrocarbons include tetrahydrofuran, dioxane and dioxolane.

The above solvents can be used singly or as a mixed solvent of two or more kinds. When they are used as a mixed solvent, they may be in a state such that they are not homogeneously mixed. Preferred examples of the single solvents include toluene, methanol and dioxane, and preferred examples of the mixed solvents include toluene-methanol, toluene-water, toluene-methanol-water, and dioxane-water.

The amount of the solvent used is in the range of usually 0.5 to 30 times by mass, preferably 1 to 20 times by mass, the amount of the nucleus-halogenated benzene dicarbaldehyde compound. If the amount of the solvent is less then 0.5 time by mass, a problem occurs in the removal of heat. On the other hand, if the amount thereof exceeds 30 times by mass, it takes long time to distill off the solvent needed to isolate the desired product, and therefore, too much solvent is undesirable.

The hydrogenation reaction in the invention is carried out by heating the reaction system to a given temperature after hydrogen is introduced into a gas phase zone or by introducing hydrogen after a gas phase zone is purged with an inert gas and the reaction system is heated to a given temperature. The reaction is carried out at a temperature of ordinary temperature to 250° C., preferably a temperature of not lower than the temperature at which the nucleus-halogenated benzene dicarbaldehyde as a substrate is melted or dissolved in a solvent.

The hydrogen partial pressure at the reaction temperature of the hydrogenation reaction is in the range of 0.2 to 5 MPa, but taking pressure resistance of a reaction apparatus into consideration, the hydrogen partial pressure is in the range of preferably 0.2 to 1.5 MPa, more preferably 0.2 to 0.9 MPa. The hydrogen gas for use in the reaction does not necessarily have to be a high-purity one and may contain an inert gas or the like exerting no particular influence on the hydrogenation reaction.

The ratio of absorption of hydrogen, i.e. the ratio of the actual amount of absorbed hydrogen in the hydrogenation reaction to the theoretical amount of absorbed hydrogen when all the nucleus-halogenated tetrafluorobenzene dicarbaldehyde represented by the formula (I) is hydrogenated into the nucleus-halogenated tetrafluoromethylbenzyl alcohol represented by the formula (II), is desirably in the range of 80 to 130%. If the ratio of absorption of hydrogen is less than 80%, the conversion ratio of the nucleus-halogenated benzene dicarbaldehyde as a raw material is low and the productivity is lowered. On the other hand, if the rate of absorption of hydrogen exceeds 130%, the hydrogenation reaction proceeds further to convert both of the aldehyde groups into methyl groups, so that such a ratio of absorption of hydrogen is undesirable.

The nucleus-halogenated methylbenzyl alcohol obtained by the preparation process of the invention is represented by the aforesaid formula (II) and corresponds to a compound wherein one of aldehyde groups of the nucleus-halogenated benzene dicarbaldehyde that is a raw material and is represented by the aforesaid formula (I) is converted into a hydroxymethyl group and the other is converted into a methyl group. Examples of such compounds include tetrafluoromethylbenzyl alcohols, such as 2,3,5,6-tetrafluoro-4-methylbenzyl alcohol, 2,4,5,6-tetrafluoro-3-methylbenzyl alcohol and 3,4,5,6-tetrafluoro-2-methylbenzyl alcohol. Of these, 2,3,5,6-tetrafluoro-4-methylbenzyl alcohol is more preferable.

The nucleus-halogenated methylbenzyl alcohol prepared by the process of the invention can be obtained by the use of a usual isolation method, such as concentration, extraction or distillation, after a catalyst is separated from the reaction liquid by filtration or the like.

EXAMPLES

The present invention is further described with reference to the following examples, but it should be construed that the invention is in no way limited to those examples.

An analytical instrument and analytical conditions used in the examples are as follows.
Gas Chromatography Analysis (Referred to as "GC Analysis" Hereinafter)
    Analytical instrument: HP6850 manufactured by HP
    Column: DB-1 manufactured by J & W, 30 m×0.32 mm×1 μm
    Column temperature: 80° C., heated up to 200° C. at 5° C./min, heated up to 290° C. at 15° C./min, held for 11 minutes
    Integrator: HP3396
    Injection temperature: 300° C.
    Detector temperature: 300° C.
    Flow rate: constant pressure 7.91 psi (68.5 ml/min, 80° C.)
    Split ratio: 50
    Detector: FID, $H_2$ 30 ml/min, Air 300 ml/min
    Carrier gas: He
Gas Chromatography Quantitative Analysis (Referred to as "GC Quantitative Analysis" Hereinafter)
    Internal standard: 1,2-dichlorobenzene Example 1

In a 100 ml autoclave, 3.0 g (14.3 mmol) of 2,3,5,6-tetrafluorobenzene-1,4-dicarbaldehyde, 27.0 g of toluene and 0.3 g of a sponge cobalt catalyst (R-400 manufactured by Nikko Rica Corporation) having been separately subjected to methanol replacement and toluene replacement in advance were placed.

First, the autoclave was purged with nitrogen at room temperature and then purged with hydrogen. Subsequently, the temperature of the autoclave was raised to 150° C., then hydrogen was fed to the autoclave with maintaining the pressure at 0.5 MPa, and the reaction was carried out at a temperature of 150° C. for 1 hour and 20 minutes. The ratio of absorption of hydrogen at this time (i.e. the ratio of the amount of absorbed hydrogen by then to the theoretical amount of absorbed hydrogen aforesaid) was 72%. The temperature of the autoclave was further raised up to 165° C. over a period of 10 minutes, then hydrogen was fed to the autoclave with maintaining the pressure at 0.85 MPa, and the reaction was further carried out at a temperature of 165° C. for 3 hours and 40 minutes. The ratio of absorption of hydrogen through the whole reaction was 106%. Then, feeding of hydrogen was terminated, and the autoclave was cooled to room temperature. Subsequently, the catalyst was filtered out, and the reaction liquid was taken out.

A small amount of a sample was withdrawn and subjected to GC analysis. As a result of the analysis, a peak of the 2,3,5,6-tetrafluorobenzene-1,4-dicarbaldehyde as a raw material was not more than the limit of detection, the formation ratio of 2,3,5,6-tetrafluoro-4-methylbenzyl alcohol was 72.7%, the formation ratio of 1,4-dimethyl-2,3,5,6-tetrafluorobenzene was 20.3%, and the formation ratio of 2,3,5,6-tetrafluorobenzene-1,4-dimethanol was 3.3%.

Example 2

In a 100 ml autoclave, 6.0 g (29.1 mmol) of 2,3,5,6-tetrafluorobenzene-1,4-dicarbaldehyde, 24.0 g of toluene and 0.6 g of a sponge cobalt catalyst (R-400 manufactured by Nikko Rica Corporation) having been separately subjected to methanol replacement and toluene replacement in advance were placed.

First, the autoclave was purged with nitrogen at room temperature and then purged with hydrogen. Subsequently, the temperature of the autoclave was raised to 120° C., then hydrogen was fed to the autoclave with maintaining the pressure at 0.5 MPa, and the reaction was carried out at a temperature of 120° C. for 3 hours and 40 minutes. The ratio of absorption of hydrogen at this time was 64%. The temperature of the autoclave was further raised up to 160° C. over a period of 30 minutes, then hydrogen was fed to the autoclave with maintaining the pressure at 0.8 MPa, and the reaction was further carried out at a temperature of 160° C. for 2 hours. The ratio of absorption of hydrogen through the whole reaction was 104%. Then, feeding of hydrogen was terminated, and the autoclave was cooled to room temperature. Subsequently, the catalyst was filtered out, and the reaction liquid was taken out.

A small amount of a sample was withdrawn and subjected to GC analysis. As a result of the analysis, a peak of the 2,3,5,6-tetrafluorobenzene-1,4-dicarbaldehyde as a raw material was not more than the limit of detection, the formation ratio of 2,3,5,6-tetrafluoro-4-methylbenzyl alcohol was 75.9%, the formation ratio of 1,4-dimethyl-2,3,5,6-tetrafluorobenzene was 14.9%, and the formation ratio of 2,3,5,6-tetrafluorobenzene-1,4-dimethanol was 3.6%.

Example 3

In a 100 ml autoclave, 6.0 g (29.1 mmol) of 2,3,5,6-tetrafluorobenzene-1,4-dicarbaldehyde, 24.0 g of toluene and 0.6 g of a sponge cobalt catalyst (R-400 manufactured by Nikko Rica Corporation) having been separately subjected to methanol replacement and toluene replacement in advance were placed.

First, the autoclave was purged with nitrogen at room temperature and then purged with hydrogen. Subsequently, the temperature of the autoclave was raised to 120° C., then hydrogen was fed to the autoclave with maintaining the pressure at 0.5 MPa, and the reaction was carried out at a temperature of 120° C. for 5 hours. The ratio of absorption of hydrogen at this time was 63%. The temperature of the autoclave was further raised up to 150° C. over a period of 20 minutes, then hydrogen was fed to the autoclave with maintaining the pressure at 0.75 MPa, and the reaction was further, carried out at a temperature of 150° C. for 5 hours and 10 minutes. The ratio of absorption of hydrogen through the whole reaction was 102%. Then, feeding of hydrogen was terminated, and the autoclave was cooled to room temperature. Subsequently, the catalyst was filtered out, and the reaction liquid was taken out.

A small amount of a sample was withdrawn and subjected to GC analysis. As a result of the analysis, a peak of the 2,3,5,6-tetrafluorobenzene-1,4-dicarbaldehyde as a raw material was not more than the limit of detection, the formation ratio of 2,3,5,6-tetrafluoro-4-methylbenzyl alcohol was 80.8%, the formation ratio of 1,4-dimethyl-2,3,5,6-tetrafluorobenzene was 8.6%, and the formation ratio of 2,3,5,6-tetrafluorobenzene-1,4-dimethanol was 6.9%.

The invention claimed is:

1. A process for preparing nucleus-halogenated methylbenzyl alcohol represented by the following formula (II), comprising hydrogenating nucleus-halogenated benzene dicarbaldehyde represented by the following formula (I);

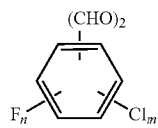

(I)

wherein m is an integer of 0 to 3, and n is an integer of 1 to 4, with the proviso that m+n is an integer of 1 to 4,

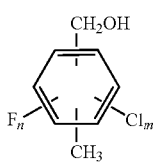

(II)

wherein m and n are the same as those in the formula (I),
wherein the hydrogenation reaction is carried out in the presence of a sponge cobalt-based catalyst,
wherein the hydrogenation reaction is carried out in two steps, in which a reaction temperature of the second step is higher than a reaction temperature of the first step, and both the reaction temperatures of the first and the second steps are not lower than the temperature at which the nucleus-halogenated benzene dicarbaldehyde is melted or dissolved in a solvent and not higher than 250° C.

2. The process for preparing nucleus-halogenated methylbenzyl alcohol according to claim 1, wherein the nucleus-halogenated benzene dicarbaldehyde is represented by the following formula (III):

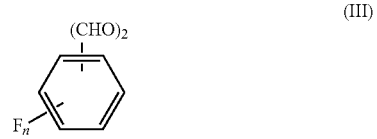

wherein n is an integer of 1 to 4, and the nucleus-halogenated methylbenzyl alcohol formed is represented by the following formula (IV):

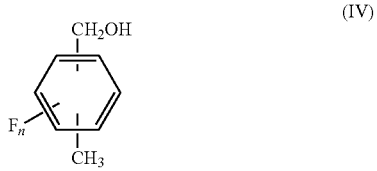

wherein n is the same as that in the formula (III).

3. The process for preparing nucleus-halogenated methylbenzyl alcohol according to claim 1, wherein the nucleus-halogenated benzene dicarbaldehyde is tetrafluorobenzene dicarbaldehyde represented by the following formula (V),

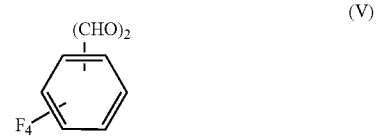

and the nucleus-halogenated methylbenzyl alcohol formed is tetrafluoromethylbenzyl alcohol represented by the following formula (VI)

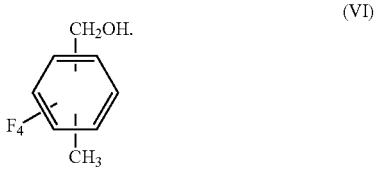

4. The process for preparing nucleus-halogenated methylbenzyl alcohol according to claim 3, wherein the tetrafluorobenzene dicarbaldehyde represented by the formula (V) is 2,3,5,6-tetrafluorobenzene-1,4-dicarbaldehyde, and the tetrafluoromethylbenzyl alcohol represented by the formula (VI) is 2,3,5,6-tetrafluoro-4-methylbenzyl alcohol.

5. The process for preparing nucleus-halogenated methylbenzyl alcohol according to claim 1, wherein the hydrogenation reaction is carried out in a solvent.

6. The process for preparing nucleus-halogenated methylbenzyl alcohol according to claim 5, wherein the hydrogenation reaction is carried out using hydrogen.

7. The process for preparing nucleus-halogenated methylbenzyl alcohol according to claim 5, wherein the solvent is a single solvent or a mixed solvent containing at least one substance selected from the group consisting of saturated aliphatic hydrocarbons, alicyclic hydrocarbons, aromatic hydrocarbons, alcohols, ethers of aliphatic hydrocarbons, ethers of alicylic hydrocarbons and water.

8. The process for preparing nucleus-halogenated methylbenzyl alcohol according to claim 7, wherein the solvent is a single solvent or a mixed solvent containing at least one substance selected from the group consisting of toluene, xylene, methanol, ethanol, dioxane, dioxolane and water.

9. The process for preparing nucleus-halogenated methylbenzyl alcohol according to claim 1, wherein the hydrogenation reaction is carried out at a hydrogen partial pressure of 0.2 to 5 MPa.

10. The process for preparing nucleus-halogenated methylbenzyl alcohol according to claim 5, wherein the amount of the solvent used in the hydrogenation reaction is in the range of 1 to 20 times by mass the amount of the nucleus-halogenated benzene dicarbaldehyde represented by the formula (I).

11. The process for preparing nucleus-halogenated methylbenzyl alcohol according to claim 6, wherein the ratio of the actual amount of absorbed hydrogen in the hydrogenation reaction to the theoretical amount of absorbed hydrogen when all the nucleus-halogenated benzene dicarbaldehyde represented by the formula (I) is hydrogenated into the nucleus-halogenated methylbenzyl alcohol represented by the formula (II) is in the range of 80 to 130%.

12. The process for preparing nucleus-halogenated methylbenzyl alcohol according to claim 2, wherein the hydrogenation reaction is carried out in a solvent.

13. The process for preparing nucleus-halogenated methylbenzyl alcohol according to claim 3, wherein the hydrogenation reaction is carried out in a solvent.

14. The process for preparing nucleus-halogenated methylbenzyl alcohol according to claim 4, wherein the hydrogenation reaction is carried out in a solvent.

15. The process for preparing nucleus-halogenated methylbenzyl alcohol according to claim 12, wherein the hydrogenation reaction is carried out using hydrogen.

16. The process for preparing nucleus-halogenated methylbenzyl alcohol according to claim 13, wherein the hydrogenation reaction is carried out using hydrogen.

17. The process for preparing nucleus-halogenated methylbenzyl alcohol according to claim 14, wherein the hydrogenation reaction is carried out using hydrogen.

* * * * *